(12) United States Patent
Valade et al.

(10) Patent No.: US 10,517,549 B2
(45) Date of Patent: Dec. 31, 2019

(54) RADIATION PROTECTION SCREEN

(71) Applicant: ARCITA, Montpellier (FR)

(72) Inventors: Frederic Valade, Montpellier (FR); Hugues Courtais, Montpellier (FR)

(*) Notice: Subject to any disclaimer, the term of this patent is extended or adjusted under 35 U.S.C. 154(b) by 0 days.

(21) Appl. No.: 15/773,654

(22) PCT Filed: Nov. 7, 2016

(86) PCT No.: PCT/FR2016/052881
§ 371 (c)(1),
(2) Date: May 4, 2018

(87) PCT Pub. No.: WO2017/077259
PCT Pub. Date: May 11, 2017

(65) Prior Publication Data
US 2018/0325473 A1    Nov. 15, 2018

(30) Foreign Application Priority Data
Nov. 5, 2015 (FR) ...................................... 15 60606

(51) Int. Cl.
*A61B 6/10* (2006.01)
*G21F 3/00* (2006.01)

(52) U.S. Cl.
CPC ................ *A61B 6/107* (2013.01); *G21F 3/00* (2013.01)

(58) Field of Classification Search
None
See application file for complete search history.

(56) References Cited

U.S. PATENT DOCUMENTS

| | | | | |
|---|---|---|---|---|
| 3,979,863 | A * | 9/1976 | Hurley | E04B 1/04 52/92.1 |
| 7,638,784 | B2 * | 12/2009 | Fox | G21F 1/125 250/505.1 |
| 7,648,273 | B2 * | 1/2010 | Manzke | A61B 6/107 250/515.1 |
| 7,829,873 | B2 * | 11/2010 | Fox | A61B 6/107 250/505.1 |
| 8,445,093 | B2 * | 5/2013 | Lemer | A61B 6/107 128/849 |
| D693,478 | S * | 11/2013 | Irick | D24/158 |

(Continued)

FOREIGN PATENT DOCUMENTS

| | | | |
|---|---|---|---|
| JP | S5757811 U | 4/1982 | |
| JP | S6337931 B2 * | 7/1988 | ................ H01J 9/46 |

(Continued)

OTHER PUBLICATIONS

International Search Report in corresponding International Patent Application No. PCT/FR/2016/052881, dated Feb. 9, 2017. 6 pages.

(Continued)

*Primary Examiner* — Andrew Smyth
(74) *Attorney, Agent, or Firm* — Leason Ellis LLP

(57) ABSTRACT

The invention relates to a radiation protection screen having two main sides. According to the invention, the radiation protection screen includes a framework which stiffens the screens and on either sides holds a pane; one of the panels being radioprotective. The invention further relates to a system including at least two screens which are or can be joined together.

11 Claims, 6 Drawing Sheets

(56) References Cited

U.S. PATENT DOCUMENTS

| | | | | |
|---|---|---|---|---|
| 8,876,380 | B2 * | 11/2014 | Mizrahi | A61B 5/0422 |
| | | | | 378/203 |
| D749,219 | S * | 2/2016 | Ballsieper | D24/158 |
| D754,348 | S * | 4/2016 | Ballsieper | D24/158 |
| 2005/0173658 | A1 * | 8/2005 | Lemer | G21F 3/00 |
| | | | | 250/515.1 |
| 2013/0330570 | A1 * | 12/2013 | Michiels | B32B 7/12 |
| | | | | 428/624 |
| 2014/0124004 | A1 * | 5/2014 | Rosenstein | A47L 9/2852 |
| | | | | 134/18 |

FOREIGN PATENT DOCUMENTS

| | | | | |
|---|---|---|---|---|
| JP | 2013007640 | A * | 1/2013 | |
| JP | 2013007640 | A | 1/2013 | |
| WO | 2009156660 | A2 | 12/2009 | |
| WO | WO-2009156660 | A2 * | 12/2009 | A61B 6/107 |
| WO | WO-2009156660 | A3 * | 2/2010 | |

OTHER PUBLICATIONS

International Preliminary Report on Patentability in corresponding International Patent Application No. PCT/FR/2016/052881, dated May 23, 2018. 6 pages.

* cited by examiner

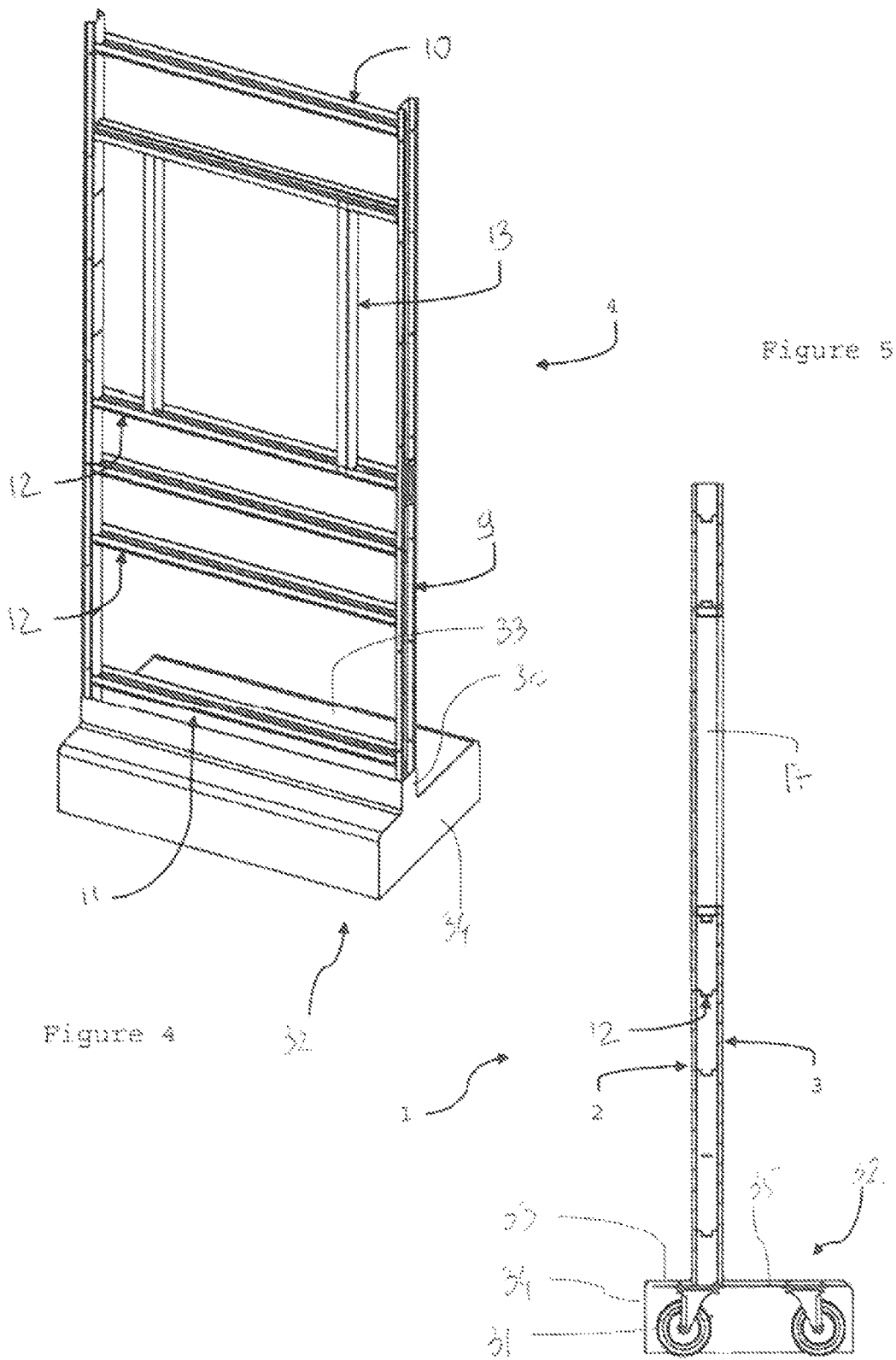

Figure 7

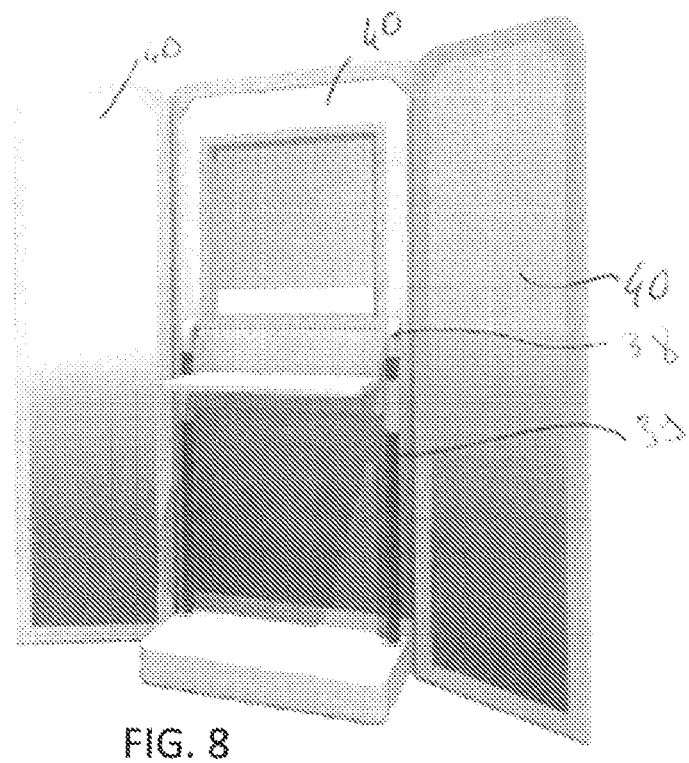
FIG. 8
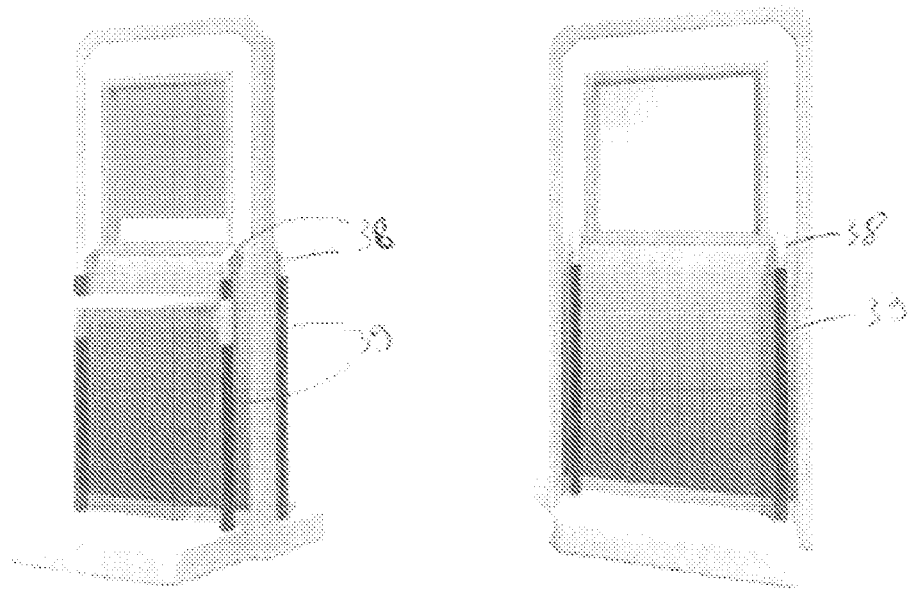
FIG. 9
FIG. 10

RADIATION PROTECTION SCREEN

CROSS-REFERENCE TO RELATED PATENT APPLICATIONS

This application is a U.S. National Phase Application under 35 U.S.C. § 371 of International Patent Application No. PCT/FR2016/052881, filed Nov. 7, 2016, and claims the benefit of priority under 35 U.S.C. Section 119(e) of French Application Serial No. 1560606, filed Nov. 5, 2015, all of which are incorporated by reference in their entireties. The International Application was published on May 11, 2017 as International Publication No. WO 2017/077259 A1.

This invention relates to a radiation protection screen.

Typically, a radiation protection screen is used to separate a person from an element emitting ionizing rays, and to protect that person from these rays.

For this purpose, a radioprotection screen includes a panel coated with a radiation protection sheet (typically a leaded sheet).

However, the rigidity of the screen comes only from the panel, and nothing can be fixed to it so as not to perforate the radiation protection sheet. In addition, in the case of mobile screen, there is no radiological protection at the wheels whose height is generally equal to about 15 cm.

The invention aims to solve the aforementioned problems, and in particular to allow the attachment of an object to the screen without altering the radiation protection sheet.

According to the invention, the radiation protection screen comprises two main faces, characterized in that it comprises a framework which stiffens the screen and which carries on each side a panel, one of the panels being radiation protective. Therefore, the screen according to this invention comprises a rigid framework which carries, on one side, a radiation protective panel and, on the other side, a panel which can be secured to an object by fixing the object to the framework. Typically, the thickness of the framework is about 5 cm.

According to a first embodiment, the frame is formed by a section assembly. As a result, the structure of the framework is particularly light. By "section", one means in particular a longitudinal structure preferably open along the longitudinal axis, such as a structure having a section "U", "L" or "V." The assembled sections are connected together to form the framework stiffening the screen.

More particularly, the framework comprises external sections and internal sections, said sections covering at least the internal sections.

According to a first variant of the first embodiment, each section is made of stainless steel. As a result, the framework is made of stainless steel.

According to a second variant of the first embodiment, each section has a generally U-shaped form, each side panel carries a side of the screen. Therefore, knowing the position of the sections, it is possible that the object is attached to the side panel that supports the non-radiation protective side.

According to a third variant of the first embodiment, the section assembly comprises an outer frame forming the outer limits of the screen.

According to a first preference of the third variant of the first embodiment, when the sections forming the outer frame have a generally U-shaped form, they are oriented so that the central branch of the U is disposed on the inside of the screen. As a result, the edge of the outer frame is formed by the opening of the U.

According to a second preference of the third variant of the first embodiment, the section assembly comprises at least one horizontal section which extends from one to the other of the two vertical sections of the outer frame. Advantageously, the section assembly comprises two parallel vertical sections which extend between two adjacent horizontal sections. As a result, the two adjacent horizontal sections and the two parallel vertical sections define a rectangular frame in the framework.

According to a second embodiment, the non-radiation protective panel comprises an inner panel fixed to the framework and an outer panel covering the inner panel. Typically, the thickness of the inner panel is about 12 to 16 mm, and that of the outer panel is about 1 to 2 mm.

According to a first variant of the second embodiment, the inner panel is a chipboard, preferably chipboard having good moisture behavior (CTBH).

According to a second variant of the second embodiment, the outer panel is a laminated panel. The laminate panel can be colored.

According to a third variant of the second embodiment, the radiation protective panel comprises a lead sheet (typically of a thickness of 1 to 2 mm) attached to the framework and a non-radiation protective panel attached to the lead sheet. Thus, the radiation protective panel includes the lead sheet that is attached to the framework, an inner panel that is attached to the lead sheet, and an outer panel that is attached to the inner panel. By its arrangement, the lead sheet provides radiation protection of the radiation protective panel.

According to a third embodiment, the radioprotection screen includes a radiation protection glazing. Typically, the radiation protection glazing is a so-called leaded glazing. Therefore, each panel includes an opening in which is disposed the radiation protection glazing.

According to a first variant of the third embodiment, the radiation protection glazing is surrounded by the two parallel vertical sections and the two adjacent horizontal sections of the advantageous mode of the second preference of the third variant of the first embodiment.

According to a second variant of the third embodiment, the radioprotection screen comprises two glazing beads, each glazing bead being disposed at the junction of the radiation protection glazing with the panels.

According to a first advantage of the second variant of the third embodiment, a first glazing bead has an L-shaped cross section, one branch of which covers the peripheral edge of the opening of one panel and the other branch bears on the framework.

According to a second advantage of the second variant of the third embodiment, a second glazing bead in the form of a simple box covering the peripheral edges of the radiation protection glazing and the opening of a panel.

According to an advantageous embodiment of the second advantage of the second variant of the third embodiment, the second windscreen covers an additional radiation protection sheet which extends into a peripheral groove formed in the radiation protective panel and which covers the peripheral rim of the radiation protection glazing, also arranged in that groove.

Preferably, the second glazing bead is fixed (by screwing) to a portion of the panel that surrounds the peripheral groove.

According to a third advantage of the second variant of the third embodiment, the glazing beads are made of aluminum.

According to a fourth embodiment, the radiation protection screen comprises wheels allowing its displacement.

According to a first variant of the fourth embodiment, the wheels are pivoting with respect to a vertical axis. As a result, the change of orientation of the screen is facilitated.

According to a second variant of the fourth embodiment, the screen comprises a base which surrounds the wheels.

According to a first advantage of the second variant of the fourth embodiment, a radiation protection film (typically a lead film) is secured to the base in order to ensure, at the level of the wheels, the continuity of the radiation protection carried out by the radiation protective panel.

According to a second advantage of the second variant of the fourth embodiment, the base comprises an upper wall which is connected to the framework, and four side walls which hang from the upper wall and which surround the wheels. Typically, the sidewalls extend from the top wall to a distance close to the ground on which the wheels rest (about 1 cm from the ground).

In addition, unlike a protection panel at the wheels, a protection by a base allows to limit the diffuse rays that can be reflected on the ground just below the panel.

According to a first preference of the second advantage of the second variant of the fourth embodiment, the radiation protection film extends, firstly, along the portion of the upper wall which extends on the side of the front face, and, on the other hand, along the side wall which is also located on the side of the front face.

According to a second preference of the second advantage of the second variant of the fourth embodiment, the upper wall and the four side walls are made of stainless steel.

According to a third preference of the second advantage of the second variant of the fourth embodiment, a skirting board connects the base to the framework in a fixed manner.

Advantageously, the skirting board is integral with the base and extends vertically upwards.

According to a third variant of the fourth embodiment, the screen comprises a handle to facilitate its grip and its movement. Advantageously, the handle is hollowed in a side edge of the screen.

According to a fifth embodiment, the screen comprises a skirting board which is fixed to the framework and which is adapted to be fixed to a floor. Advantageously, the skirting board is made of stainless steel in order to withstand the possible shocks that it could undergo once the screen has been installed.

According to a sixth embodiment, the screen comprises a peripheral covering which forms its outer limit.

According to a first variant of the sixth embodiment, the peripheral casing covers the outer peripheral edge of the two sections of the screen.

According to a second variant of the sixth embodiment, the peripheral casing with a generally U-shaped form, each side branch of which covers the outer peripheral edge of a panel and whose central branch forms the corresponding edge of the screen.

According to a third variant of the sixth embodiment, the peripheral casing is made of aluminum.

According to the seventh embodiment, the panel which is not radiation protective carries a tablet attached to the frame. Advantageously, the tablet comprises a fixed part fixed to the frame and a movable part articulated to the fixed part.

Other features and advantages of this invention will appear in the detailed description of two examples given by way of non-limiting example and illustrated in the accompanying drawings in which:

FIG. 4 is a perspective view of the framework of the screen of FIG. 3, framework at the bottom of which is fixed a skirting board and a base;

FIG. 5 is a vertical sectional view through the protective glazing of the screen of FIG. 3;

Figure 7:
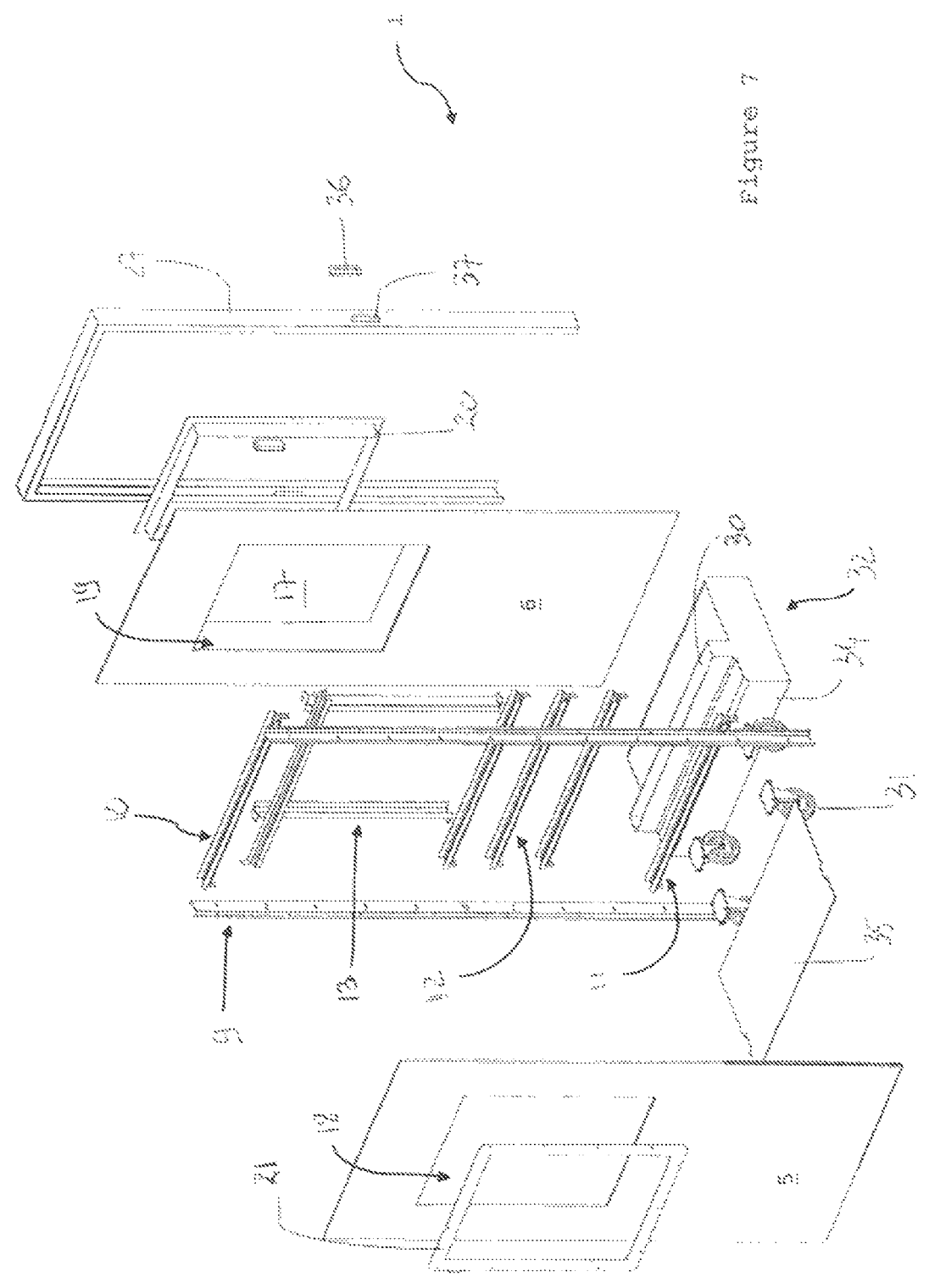

FIG. 7 is an exploded perspective view of the screen of FIG. 3;

FIG. 8 is a perspective view of a system according to a variant of the invention; and FIGS. 9 and 10 are perspective views of a central screen of a system according to the invention.

FIGS. 1 and 3 show in perspective two examples of radiation protection screen 1 according to this invention.

Figures 1, 2:
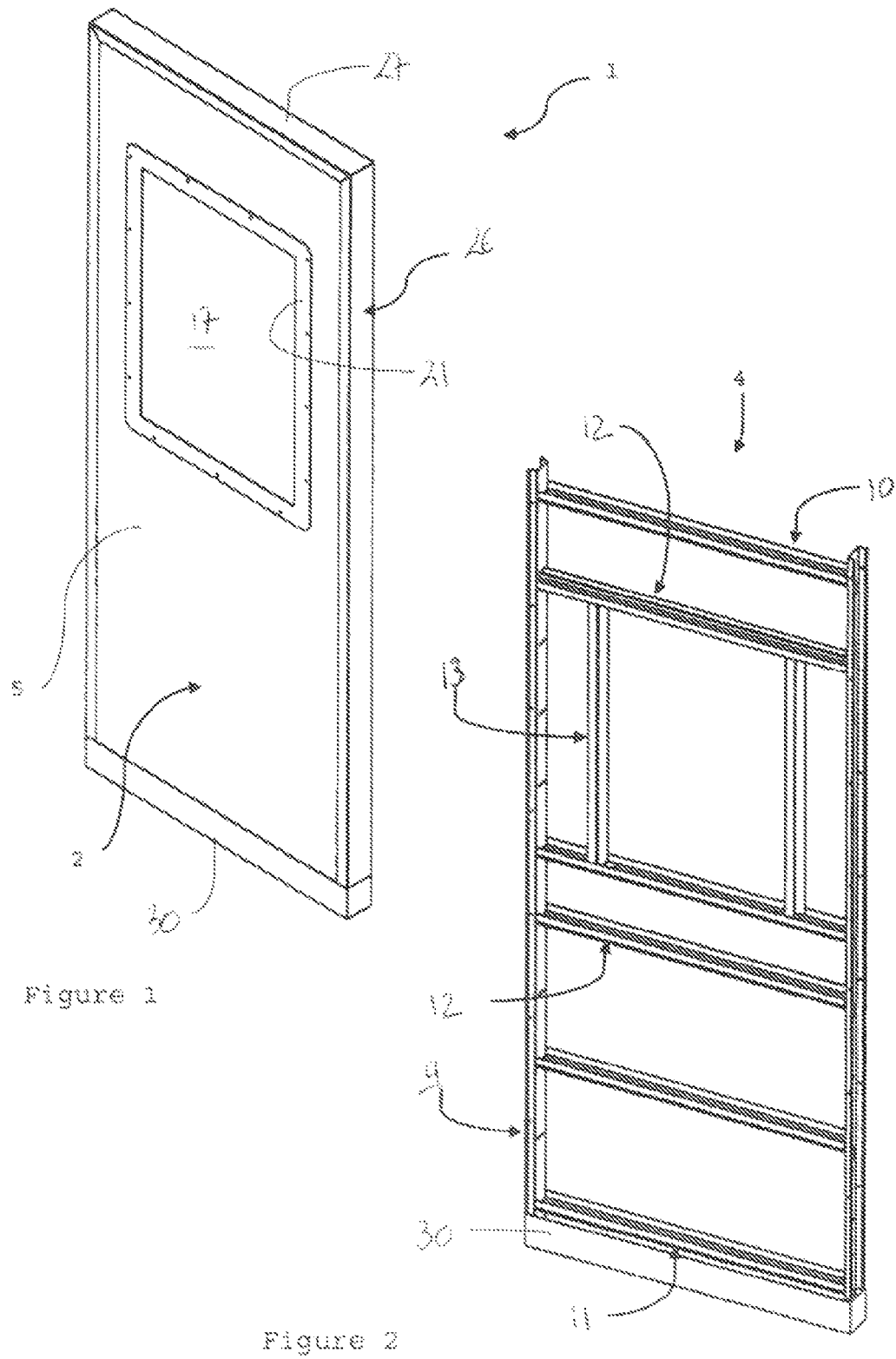
FIG. 1 is a perspective view of a first example of a screen according to this invention.
FIG. 2 is a perspective view of the frame of the screen of FIG. 1, framework at the bottom of which is fixed a skirting board.
Figure 3:
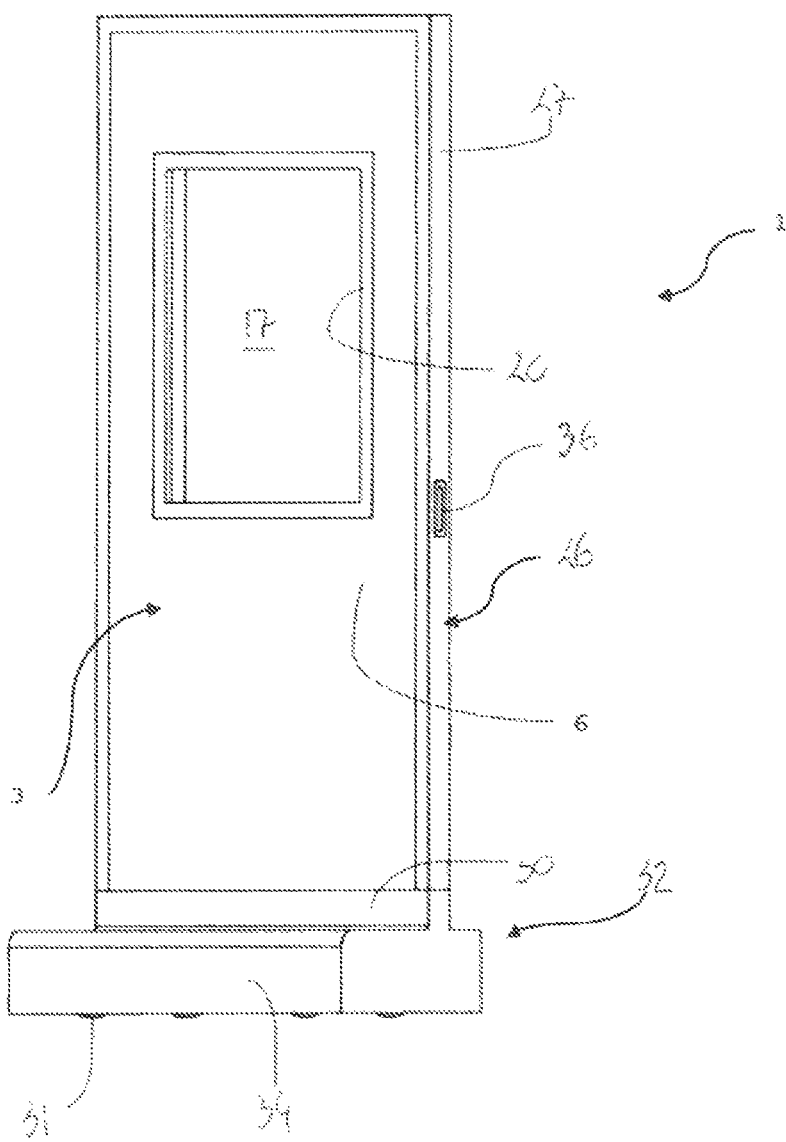
FIG. 3 is a perspective view of a second example of a screen according to this invention.
Figure 6:
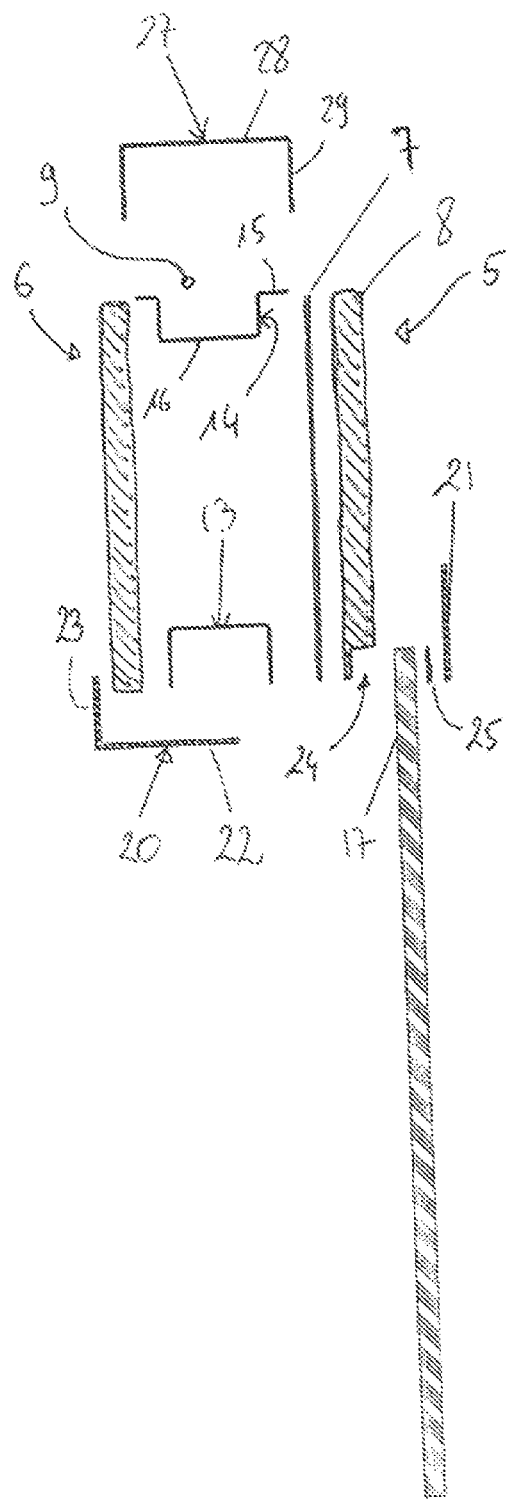
FIG. 6 is a sectional view of the portion of the screen located at the glazing beads.

Each radiation protection screen 1 comprises two main faces 2, 3: a front face 2 intended to be on the source side emitting ionizing radiation, and a rear face 3 intended to be on the side of the people to protect from the ionizing radiation.

According to the invention, the radiation protection screen 1 comprises a framework 4 which stiffens it and which carries a front panel 5 on the side of the front panel 2, and a rear panel 6 on the side of the rear panel 3. Here, the front panel 5 is a radiation protective panel and the rear panel 6 is a non-radiation protective panel. In the present examples, each radiation protection screen 1 has a height of 2 meters and a width of 0.8 meters, and the distance between the front face 2 of the rear face 3 is 72 millimeters.

The radiation protective panel 5 is formed by a radiation protection sheet 7 (typically a leaded sheet) which is attached to framework 4 and a non-radiation protective panel 8 (typically the same panel as the rear panel 6) which is attached to the radiation protection sheet 7. The thickness of the radiation protection sheet 7 is approximately 1 to 2 millimeters.

The non-radiation protective rear panel 6 and the non-radiation protective panel 8 forming part of the front radiation protective panel 5 comprise an inner panel and an outer panel. The inner panel is attached to the lead sheet 7 (in the case of the radiation protective front panel 5) or to framework 4 (in the case of the non-radiation protective rear panel 6). The outer panel covers the inner panel. Typically, the inner panel is a chipboard (preferably chipboard with good moisture behavior) and its thickness is about 12 to 16 millimeters. Typically, the outer panel is a laminated panel and its thickness is about 1 to 2 millimeters.

Framework 4 is 12-tenths stainless steel and is formed by an assembly of sections 9, 10, 11, 12, 13 which gives strength and lightness to the radiation protection screen 1 (each section is made of stainless steel).

Framework 4 is 12-tenths stainless steel and is formed by an assembly of sections 9, 10, 11, 12, 13 which gives strength and lightness to the radioprotection screen 1 (each section is made of stainless steel).

In particular, framework 4 comprises external sections 9, 10, 11 and internal sections 12, 13. Sections 5, 6 cover at least internal sections 12, 13. Preferably, the internal sections are arranged between sections 5, 6.

Each section 9, 10, 11, 12, 13 has a generally U-shaped form, of which each side panel carries a panel 5, 6. Here, the width of each side panel is about 20 millimeters and the width of the central branch is about 50 millimeters.

Section 9, 10, 11, 12, 13 assembly comprises a rectangular outer frame forming the outer boundaries of the radiation protection screen 1. In this case, this outer frame comprises two vertical sections 9 and two horizontal sections 10, 11 connecting the two vertical sections 9 (an upper horizontal section 10 located near the upper ends of the two vertical sections 9, and a lower horizontal section 11 disposed near the lower ends of the two vertical sections 9).

Here, vertical sections 9 of the outer frame have a U-shaped form, each lateral branch 14 carrying a wheelbase 15 which is parallel to the central branch 16 and which is directed opposite the other lateral branch 14. The central branch 16 is disposed on the inside of the radiation protection screen 1 and, therefore, the edge of the outer frame is formed by the opening of the U. Each wheelbase 15 has a width of about 10 millimeters.

Section 9, 10, 11, 12, 13 assembly also comprises at least one internal horizontal section 12 which extends from one to the other of the two vertical sections 9 of the outer frame (here, four internal horizontal sections 12).

In the present examples, the central branch of the U of all the horizontal sections 10, 11, 12 (including those of the outer frame) is formed by two horizontal walls which are in line with one another so as to form the major part of the central branch, the two horizontal walls being connected to each other by a central U-shaped connecting segment. The central U-shaped segment comprises a central branch and two lateral branches. The central branch of the U-shaped central link segment is parallel to the two horizontal walls which form the major part of the central branch of horizontal section 10, 11, 12 in U. The two lateral branches of the central link segment are parallel to each other and with the two lateral branches of horizontal section 10, 11, 12 in U. Each horizontal wall carries at one end a lateral branch of horizontal section 10, 11, 12 U which extends in a first direction, and at a second end a lateral branch of the central connecting segment which extends in a second direction opposite to the first direction.

The assembly of sections 9, 10, 11, 12, 13 also comprises two parallel internal vertical sections 13 which extend between two adjacent internal horizontal sections 12. In the present examples, the two internal vertical sections 13 have a U-shape and have, at each of their longitudinal end, a connecting wall which is carried by the central branch of the internal vertical section 13 and which is oriented in the opposite direction to that of the lateral branches of the inner vertical section 13. The two connecting walls of the two internal vertical sections 13 allow to fix these two sections 13 to two adjacent internal horizontal sections 12. As a result, the two adjacent internal horizontal sections 12 and the two internal vertical sections 13 define a rectangular frame in framework 4.

Panels 5, 6 (more precisely the inner panels of panels 5, 6) are attached to the lateral branches of the sections of framework 4 and their edges (more precisely the edges of the inner and outer panels and the radiation protection sheet 7 of sections 5, 6) abut against the wheelbases 15 of the two vertical sections 9 of the outer frame of framework 4.

Radiation protection screen 1 comprises a radiation protection glazing 17. Typically, this radiation protection glazing 17 is a so-called leaded glazing. It has a thickness of 8.5 millimeters (corresponding to a thickness of 2.2 millimeters of lead equivalent).

Each panel 5, 6 comprises an opening 18, 19 situated at the level of radiation protection glazing 17. Here, radiation protection glazing 17 is situated at the level of the two internal vertical sections 13 and of the two adjacent horizontal sections 12 (more precisely, the U-shaped openings of these four sections 12, 13 are oriented towards the edges of radiation protection glazing 17).

The radiation protection screen comprises two glazing beads 20, 21 (in this case made of aluminum) which are arranged at the junction of the radiation protection glazing 17 with the openings 18, 19 of panels 5, 6 and which, when assembled, form a U-shaped section whose central branch is arranged against and each lateral branch encircles a panel 5, 6 at its opening 18, 19.

A first glazing bead 20 has a L-shaped cross-section, a first bar 22 of which (the one forming the central branch of the U of the two glazing beads 20, 21 assembled) encircles internal vertical sections 13 and adjacent horizontal sections 12 and a second 23 bar covers the peripheral edge of opening 18 of non-radiation protective rear panel 6. The first bead 20 is fixed, on the one hand, to the two internal vertical sections 13 and to the two adjacent horizontal sections 12, and, on the other hand, to non-radiation protective rear panel 6.

The second glazing bead 21 is a simple box that covers the peripheral edge of the opening 19 of radiation protective front panel 5. In order to ensure a continuity of the radiation protection at the level of radiation protection glazing 17, the inner panel of radiation protective front panel 5 comprises all along the edge of its opening 19, a groove 24. In this groove 24 are arranged the glazing of radiation protection 17 and an additional radiation protection sheet 25 (typically leaded sheet). The additional radioprotection sheet 25 covers the portion of radiation protection glazing 17 disposed in groove 24. Second glazing bead 21 completely covers the additional radiation protection sheet 25 and the solid part of the inner panel surrounding groove 24. As a result, second glazing bead 21 can be fixed to radiation protective front panel 5 by screwing without breaking the continuity of radiation protection (the screws pass through second glazing bead 21 and the solid part of the inner panel which surrounds groove 24).

Radiation protection screen 1 comprises a peripheral casing 26 (here, aluminum) which forms its edge and its outer limit. Peripheral casing 26 covers the outer peripheral edges of the two panels 5, 6 and is fixed to frame 4.

In the present embodiments, for each upper and lateral outer peripheral edge, peripheral casing 26 is a section 27 having the shape of a U with a central panel 28 and two lateral branches 29, each side panel 29 covering the edge outer peripheral of a panel 5, 6, and central branch 28 forming the edge of radiation protection screen 1.

For the lower peripheral edge, peripheral casing 26 is formed by a skirting board 30.

In the first example, skirting board 30 is adapted to be fixed to a floor so as to make radiation protection screen 1 fixed.

In the second example, skirting board 30 is also attached to wheels 31 so as to make the radiation protection screen 1 movable. Here, each wheel 31 is pivotally mounted relative to skirting board 30 along a vertical axis to facilitate the change of orientation of the radiation protection screen 1. From skirting board 30 hangs a base 32 (here, stainless steel) which surrounds wheels 31. This base 32 comprises a horizontal upper wall 33 which is connected to skirting board 30 and framework 4, and four vertical side walls 34 which hang from upper wall 33 and which surround wheels 31. Typically, side walls 34 extend from upper wall 33 to a distance close to the ground (about 1 centimeter from the ground). In the second example, wheels 31 are fixed to the underside of a fixing plate 35 whose upper face is fixed to the lower face of upper wall 33.

In the second example, in order to ensure radiation protection at the level of wheels 31, base 32 comprises a radiation protection film (typically a leaded sheet). The radiation protection film of base 32 and the radiation protection sheet of radiation protective panel 5 are arranged in such a way as to ensure a continuity of the radiation protection. Here, the radiation protection sheet film extends along the portion of upper wall 33 which extends on the side of front face 2, and along side wall 34 which is also located on the side of front face 2. The radioprotection film is covered by the front part of upper wall 33 and front side wall 34.

Finally, in order to easily direct the movement of radiation protection screen 1, the latter comprises at least one handle 36 (here, two handles 36). In this case, each handle 36 is a hollow handle which is arranged in an orifice 37 made in the central branch of each section 27 associated with a lateral outer circumferential edge of radiation protection screen 1.

It is also possible to provide solid handles 38, for example tubular.

Handles 38 preferably include an antibacterial material on their surface. For example, the handles comprise a surface metallized with ferrous or non-ferrous metals and cold-solidified.

In addition to its properties conferring rigidity without burdening the radiation protection screen, framework 4 also makes it possible to securely fix an object to the non-radiation protective rear panel 6. This fixation is done by resting on at least one section 9, 10, 11, 12, 13 of framework 4. The fixed object can thus be a horizontal shelf. In order to limit the space requirement, the tablet may comprise a first part fixed to framework 4 and a second part articulated to the first part. In the case of a fixed radiation protection screen 1, the fixed object can be a worktop (which can also be supported on other supports).

According to a variant, at least one, preferably two support arms 39 may be attached to framework 4 or to rear panel 6. Support arm 39 may serve as a handle 38.

Furthermore, in order to avoid tilting of movable radiological protection screen 1 because of the weight of the object which is fixed there and of the material which rests on it, upper wall 33 of base 32 extends more on the side of the rear face 3.

Finally, the presence of framework 4 also makes it possible to have a radiation protection screen 1 comprising passages making it possible to pass cables (for example electrical cables) and to have power outlets for electrical equipment (in particular the one resting on the objects fixed to the non-radiation protective rear panel 6.

In addition, the screen may include at least one sticker 40 on one or both sides. Sticker 40 can be used to customize the screen, affix a mark or decorate the screen. Preferably, the sticker is antimicrobial.

The invention further relates to a system comprising at least two screens connected or capable of being coupled together, at least one of which is as previously described.

Preferably, the system comprises a central screen carrying one or more, preferably two, side screens. The extra screens protect more people, especially up to 4 to 5 people with two side screens.

According to a variant, the central screen comprises a base and wheels and preferably, the side screens do not include any wheel.

According to one variant, the screens are coupled together by means of at least one hinge. Preferably, the hinge comprises a radiation protective element, or a radiation protective panel comprises an extension covering the hinge.

Preferably, the screen or the system comprises a mechanism configured to vary the height of the screen or of the system relative to the ground. For example, an elevation of a few millimeters makes it easier to move while a lowering so as to be in contact with the ground makes it possible to improve radiation protection.

The invention claimed is:

1. A radiation protection screen comprising two main faces, characterized in that it comprises:
    a framework which stiffens the screen and which has two panels on different sides, one of the two panels being radiation protective, another of the two panels being non-radiation protective;
    a peripheral casing which forms the edge of screen and covers lower peripheral edges of the two panels, the peripheral casing including a skirting board which covers the lower peripheral edge of the two panels,
    wheels for moving the radiation protection screen fixed to the skirting board and a base including a radiation protection film fixed to the skirting board and surrounding the wheels.

2. The radiation protection screen according to claim 1, characterized in that framework is formed by an assembly of sections.

3. The radiation protection screen according to claim 2, characterized in that each section has a generally U-shaped form, each section having one of the two panels.

4. The radiation protection screen according to claim 1, characterized in that it comprises a radiation protection glazing.

5. The radiation protection screen according to claim 1, wherein the two panels are parallel to each other.

6. The radiation protection screen according to claim 1, wherein the base comprises a horizontal upper wall which is connected to skirting board and framework, and four vertical side walls which hang from upper wall and which surround wheels.

7. The radiation protection screen according to claim 1, wherein the radiation protection film of the base and the radiation protective panel are arranged in such a way as to ensure a continuity of the radiation protection.

8. The radiation protection screen according to claim 1, characterized in that a shelf is attached to framework on a side having the non-radiation protective panel.

9. The radiation protection screen according to claim 1, characterized in that framework comprises external sections and internal sections, said two panels covering at least the internal sections.

10. A system comprising at least two radiation protection screens connected or capable of being coupled together, of which at least one of the two radiation protection screens is according to claim 1.

11. A system according to claim 10, wherein said screens are coupled by means of at least one hinge.

* * * * *